United States Patent [19]

Chung et al.

[11] Patent Number: 4,849,357
[45] Date of Patent: Jul. 18, 1989

[54] METHOD FOR THE PREPARATION OF A HYDROPHOBIC ENZYME-CONTAINING COMPOSITION AND THE COMPOSITION PRODUCED THEREBY

[75] Inventors: Koo-Heung Chung, Granger; Francis H. Verhoff, Goshen, both of Ind.

[73] Assignee: Miles Inc., Elkhart, Ind.

[21] Appl. No.: 916,726

[22] Filed: Oct. 8, 1986

[51] Int. Cl.$^4$ .................. C12N 9/96; C12N 11/04; C11D 17/00
[52] U.S. Cl. .................. 435/188; 435/182; 435/187; 252/174.12; 524/450; 524/457; 524/458

[58] Field of Search .............. 435/182, 187, 188, 264, 435/263; 252/174.12, DIG. 12; 424/450, 457, 458

[56] References Cited

U.S. PATENT DOCUMENTS

| | | | |
|---|---|---|---|
| 4,196,187 | 4/1980 | Dannelly et al. | 424/21 |
| 4,661,452 | 4/1987 | Markucsen et al. | 435/187 |
| 4,707,287 | 11/1987 | Herdeman et al. | 252/91 |

Primary Examiner—Robert Wax
Assistant Examiner—P. Carse
Attorney, Agent, or Firm—Jerome L. Jeffers

[57] ABSTRACT

A enzyme-containing solid composition is prepared by a process comprising removing the solvent from a mixture of a water-soluble enzyme, a water-insoluble metal salt of a fatty acid and an organic solvent.

25 Claims, No Drawings

METHOD FOR THE PREPARATION OF A HYDROPHOBIC ENZYME-CONTAINING COMPOSITION AND THE COMPOSITION PRODUCED THEREBY

FIELD OF THE INVENTION

The invention relates to a method for the preparation of a composition which comprises a hydrophilic enzyme which is modified to impart hydrophobic characteristics thereto. The enzyme-containing composition is useful for the enzymatic modification of a hydrophobic substrate in an aqueous environment.

BACKGROUND OF THE INVENTION

Enzymes are proteins which catalyze a wide variety of chemical reactions, many of great commercial importance. Enzymes are generally classified according to the type of reaction which they catalyze, e.g., hydrolases are enzymes that catalyze the addition of the elements of water across the bond that is cleaved, e.q., an ester or peptide linkage. Commercially-important hydrolases include proteases which are employed in laundry detergents, polysaccharidases which control slime in industrial process waters, and lipases which are employed to transesterify fats and oils. Cellulases and ligninolases can be employed in wood fiber production and bleaching.

The hydrophilicity, or high water-solubility, of many of these enzymes often reduces their utility in hydrophobic (lipophilic) media and their reactivity with hydrophobic substrates. The biocatalytic reaction is inefficient due to phase separation between the two reactants. Either the enzyme is introduced into an aqueous phase in which the hydrophobic substrate is insoluble, or neither the enzyme nor the hydrophilic substrate can dissolve or disperse in the hydrophobic medium. For example, the removal of oily or fatty soils from food processing equipment cannot be readily accomplished with aqueous lipase solutions due to the lack of affinity of the enzyme for the hydrophobic residues. Furthermore, even in the presence of stabilizers, the activity of free enzymes often decreases rapidly in aqueous media.

One attempt to partly circumvent these problems involves contacting aqueous dispersions or solutions of the target substrate with enzymes which have been immobilized by physical adsorption or covalent bonding to water-insoluble carriers such as cellulose fibers or silica beads. Enzymes have also been immobilized by entrapping them in polymeric matrices. See K. Yokozeki et al., European J. Appl. Microbiol. Biotechnol., 14, 1, (1982). Circulation of a stream of the substrate or a dispersion thereof through a zone containing the immobilized enzyme can reduce losses due to the addition of free enzymes to a process water stream. However, immobilization or entrapment of enzymes can reduce their activity. Furthermore, the substrate matrix can further reduce the efficiency of enzyme-substrate contact.

Therefore, a need exists for a method to selectively decrease the water-solubility of hydrophilic enzymes such as hydrolases, and thereby to increase the efficiency of enzymatic interaction with hydrophobic substrates in aqueous media.

SUMMARY OF THE INVENTION

The present invention provides a method for increasing the lipophilicity of a water-soluble enzyme, such as a hydrolase, comprising mixing the enzyme with the metal salt of a water-insoluble fatty acid in the presence of an organic solvent and removing the solvent. A dry solid composition results which exhibits reduced hydrophilicity while retaining essentially all of its initial enzymatic activity.

Although the hydrophile-lipophile balance number (HLB) exhibited by the present composition is a function of the type and relative amount of the fatty acid salt or salts which are combined with the enzyme, the compositions are immiscible in water. In the presence of an excess of water, the enzyme gradually dissociates from the composition, e.g., over about 0.25–3.0 hrs. Although the enzyme composition can be physically dispersed in aqueous systems to a limited extent, the dispersion of the composition and the release of the enzyme therefrom can be enhanced and controlled by incorporating suitable surfactants into the composition.

Therefore, the composition of the present invention entrains the enzyme in an environment which can adjust its HLB so that it is compatible with a wide variety of hydrophobic media and/or subtrates. The present invention provides a composition that will associate and enzymatically react with hydrophobic substrates in aqueous solution, or that will react with hydrophilic substrates (starches, celluloses and proteins) entrapped by or dispersed in hydrophobic substances in aqueous solution.

The modified enzymes of the invention are stable, non-toxic and inexpensive to prepare. Furthermore, the changes in the molecular structure of enzymes which are necessarily involved in immobilization of enzymes by covalent bonding are avoided.

In reference to the present invention, all percentages and parts are by weight unless otherwise noted. The term "water insoluble" is defined herein to include materials which are essentially or practically water-insoluble, e.g., which exhibit only slight water-solubility.

DETAILED DESCRIPTION OF THE INVENTION

The present compositions are prepared by mixing one or more hydrophilic enzymes with one or more water-insoluble fatty acid metal salts in the presence of an organic solvent. Although not intending to be bound by any theory of action, it is believed that the solvent causes the carbon chain of the fatty acid to unfold. When the solvent is removed from the mixture, the chain refolds and intertwines with the enzyme. This interaction may act to physically complex the enzyme and the fatty acid, so that the fatty acid acts as a hydrophobic carrier for the enzyme. As further described hereinbelow, the effective HLB of the resultant solid composition can be varied by changing the ratio of enzyme to the fatty acid salt, by varying the fatty acid salt carrier, or by optionally incorporating various amounts of surfactant into the composition.

Enzyme

Any hydrophilic, or water-soluble, enzymes can be employed in the composition and method of the present invention, including hydrolases, oxidoreductases (glucose oxidase, xanthic oxidase, amino acid oxidase), transferases (transglycosidases, transphosphorylases, phosphomutases, transaminases, transmethylases, transacetylases), desmolases (ligases, lyases) and isomerases (racemases, cis-trans isomerases) and the like. Of these enzymes, the hydrolases are preferred for use in the present compositions. Hydrolases catalyze a wide variety of hydrolytic reactions, including (a) the cleavage of ester linkages (esterases such as lipases, phosphoric mono- and di-esterhydrolases such as phosphatases), (b) the cleavage of glycosides (carbohydrases such as polysaccharidases, e.g., levan hydrolase, cellulase, amylase, ligninolase and the like). (c) the cleavage of peptide linkages (proteases such as alpha-aminopeptide amino acid hydrolases, alpha-carboxypeptide amino acid hydrolases) and the cleavage of nucleic acids (nucleases).

The hydrolases catalyze the addition of water to the substrate, i.e., the soils with which they interact, and thus, generally, cause a breakdown or degradation of such a substrate. This is particularly valuable in cleaning procedures. Particularly preferred hydrolases are the proteases, esterases, carbohydrases and nucleases, with the proteases having the broadest range of soil degradation capability. Mixtures of the enzymes may be used if desired.

The proteases catalyzes the hydrolysis of the peptide linkage of proteins, polypeptides and related compounds to free amino and carboxyl groups and thus break down the protein structure in soil. Specific examples of proteases suitable for use in this invention are pepsin, trypsin, chymotrypsin, collaqenase, keratinase, elastase, subtilisin, BPN' (a bacterial protese derived from Bacillus Subtilis N'), papalin, bromelin, carboxy peptidase A and B, amino peptidase, asperqillopeptidase A and aspergillopeptidase B. Preferred proteases are serine proteases which are active in the neutral to alkaline pH range and are produced from microorganisms such as bacteria, fungi or mold. The serine proteases which are procured by mammalian systems, e.q., pancreatin, are useful in acidic media.

Esterases catalyze the hydrolysis of an ester, such as lipid soil, to an acid and an alcohol. Specific examples of the esterases are gastric lipase, pancreatic lipase, plant lipases, phospholipases, cholinesterases and phosphatases. Esterases function primarily in acidic systems.

Carbohydrases catalyze the breakdown of carbohydrate soil. Specific examples of this class of enzymes are maltase, saccharase, amylases such as alpha-amylase and amyloglucosidase, cellulase, pectinase, lysozyme, α-glycol-sidase and β-glycosidase. They function primarily in acidic to neutral systems.

The commercially-available enzyme products are useful and are generally dry powdered products comprising 2% to 80% of active enzymes in combination with an inert powdered vehicle such as sodium, ammonium or calcium sulphate or sodium chloride, clay or starch as the remaining 98-20%. Active enzyme content of a commercial product is a result of manufacturing methods employed and is not critical herein so long as the final complex has the desired enzymatic activity. For an extensive listing of commercially-available hydrolases, see Sigma Chemical Company Catalog of Biochemical and Organic Compounds, St. Louis, MO (February, 1986) at pages 33-34, the disclosure of which is incorporated by reference herein.

Preferred enzymes for incorporation in the present compositions include esterases, carbohydrases or mixtures thereof.

Fatty Acid Salt

The water-insoluble fatty acid metal salts useful in the present invention can be represented by the general formula:

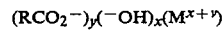

$$(RCO_2^-)_y(^-OH)_x(M^{x+y})$$

wherein R is an about $C_6$–$C_{30}$ alkyl group, preferably a $C_8$–$C_{22}$ alkyl group, wherein about 0–3 double bonds are present in the alkyl group; x is 0 or a natural number, y is a natural number and x+y is the valency of the metal (M). Preferably, x is 0–2 and y is 1–3, most preferably x is 0–1.

Therefore, a suitable fatty acid anion group ($RCO_2^-$) is palmitate, strerate, oleate, myristate, cocoate, laurate, caprylate, undecylenate, myristolenate, palmitolenate, petroselate, erucate, grassidate, geranate, linoleate, linolenate and the like. For other useful monobasic aliphatic fatty acids, see Organic Chemistry, F. C. Whitmore, ed., Dover Pubs., Inc., NY, (2d ed., 1951), the disclosure of which is incorporated by reference herein.

Any metal cation can be employed in the salt as long as the cation is chosen so that the metal salt of the fatty acid is water-insoluble. Examples of the metal cations that may be employed are the alkaline earth metal cations such as $Ca^{+2}$ and $Mq^{+2}$, and $Al^{+3}$. Of these three, $Al^{+3}$ is preferred because its fatty acid salts are more hydrophobic than the fatty acid salts of $Ca^{+2}$ and $Mq^{+2}$. Commercially-available fatty acid salts of these metals include magnesium oleate and stearate, aluminum stearate, palmitate and oleate, and calcium stearate, palmitate and oleate, as well as the hydroxylated derivatives thereof. More particularly, it has been found that $Al(OH)(stearate)_2$, hereinafter referred to as aluminum distearate, and $Al(OH)(oleate)_2$, hereinafter referred to as aluminum dioleate, may be very advantageously employed in the method and composition of the present invention.

Organic Solvent

The organic solvent must be chosen so that (1) it will not appreciably denature the enzyme and (2) it will substantially dissolve the fatty acid salt. The enzyme compatibility with a driven solvent can be readily determined by one skilled in the art without undue experimentation by adding a portion of solvent to the medium during an enzyme assay, such as the assays described hereinbelow, and measuring the decrease, if any, in enzymatic activity as compared to the activity determined by an assay performed without the addition of the solvent.

More particularly, the organic solvent may be selected from the group consisting of alcohols, ketones, aromatics, alkyl halides and ethers. Useful alcohols include 3-methyl-3-hexanol, 2-octanol, tert-butanol, n-butanol, 2-methylcyclopentanol, n-propanol, isopropanol, ethanol, geraniol, n-hexadecanol, n-decanol, or n-heptanol. Useful ketones include methyl ethyl ketone or acetone. Useful aromatic solvents include benzene, pyridine, aniline, or toluene; useful alkyl halides include carbon tetrachloride, chloroform, or methylene chloride; and useful ethers include diethyl ether, methyl ethyl ether, diphenyl ether, or anisole.

Surfactant

A surfactant or wetting agent may be included in the composition of the present invention in a weight amount from 0% to about 10% based on the combined weight of the enzyme and fatty acid salt. The optional surfactant must be chosen so that it will not appreciably denature the enzyme. Whether or not it exhibits an inhibitory effect on the enzyme can be easily determined by one skilled in the art without undue experimentation.

The surfactant counteracts the water repellency of the fatty acid salt. Thus, the degree of water dispersibility of the complex can be varied depending on the amount of surfactant which is incorporated therein. Furthermore, when a surfactant is incorporated in the composition, the dissociation rate of the complex is increased and thus the rate of solubility of the enzyme in the water increases. A complex without any surfactant incorporated therein may take up to an hour or more for about half of the enzyme to leach therefrom when the complex is quiescent in water. On the other hand, incorporation of as little as about 1–2% by weight of a surfactant based on the combined weight of enzyme and fatty acid salt may cause essentially all of the enzyme to leach from the complex into the water in about one hour or less.

Of the various classes of surfactants, nonionic and anionic surfactants or mixtures thereof are preferred for use in the present invention.

Preferred nonionic surfactants include the condensation products of ethylene oxide with a hydrophobic polyoxyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include certain of the commercially-available Pluronic TM surfactants (BASF Wyandotte Corp., Parsippany, NJ), especially those in which the polyoxypropylene ether has a molecular weight of about 1500–3000 and the polyoxyethylene content is about 35–55% of the molecule by weight, i.e., Pluronic TM L-62.

Other preferred nonionic surfactants include the condensation products of $C_8$–$C_{22}$ alkyl alcohols with 2–50 moles of ethylene oxide per mole of alcohol. Examples of compounds of this type include the condensation products of $C_{11}$–$C_{15}$ fatty alkyl alcohols with about 3–45 moles of ethylene oxide per mole of alcohol which are commercially-available as the Poly-Tergent TM SLF series from Olin Chemicals or the Tergitol TM series from Union Carbide, i.e., Tergitol TM 15-S-20, 15-S-12, and 15-S-15, which are formed by condensing a $C_{11}$–$C_{15}$-fatty alcohol mixture with an average of 20, 12 and 15 moles of ethylene oxide, respectively. These compounds are also available from Shell Chemical Co. as Neodol TM 25-3, 25-7 and 25-9, which are the condensation products of $C_{12}$–$C_{15}$ fatty alkyl alcohols with about 3, 7 and 9 moles of ethylene oxide, respectively.

Other nonionic surfactants which may be employed include the ethylene oxide esters of $C_6$–$C_{12}$ alkyl phenols such as (nonylphenoxy)polyoxyethylene ether. Particularly useful are the esters prepared by condensing about 8–12 moles of ethylene oxide with nonylphenol, i.e. the Igepal TM CO series (GAF Corp., New York, NY).

Another useful class of nonionic surfactant is the silicone-glycol copolymers. These surfactants are prepared by adding poly(lower)alkylenoxy chains to the free hydroxyl groups of dimethylpolysilioxanols and are available from the Dow Corning Corp. as Dow Corning 190 and 193 surfactants (CTFA name: dimethicone copolyol).

Other useful nonionics include the ethylene oxide esters of alkyl mercaptans such as dodecyl mercaptan polyoxyethylene thioether, the ethylene oxide esters of fatty acids such as the lauric ester of polyethylene glycol and the lauric ester of methoxypolyethylene glycol, the ethylene oxide ethers of fatty acid amides, the condensation products of ethylene oxide with partial fatty acid esters of sorbitol such as the lauric ester of sorbitan polyethylene glycol ether, and other similar materials, wherein the mole ratio of ethylene oxide to the acid, phenol, amide or alcohol is about 5–50:1.

Useful anionic surfactants include the ammonium and alkali metal salts of sulfated ethylenoxy fatty alcohols (the sodium or ammonium sulfates of the condensation products of about 1–4 moles of ethylene oxide with a $C_8$–$C_{22}$ fatty alcohol, such as a $C_{12}$–$C_{15}$ n-alkanol, i.e., the Neodol TM ethoxysulfates, such as Neodol TM 25-3S, Shell Chemical Co.; n-$C_{12}$–$C_{15}$-alkyl(OEt)-$_3$OSO$_3$Na; and Neodol TM 25-3A, the corresponding ammonium salt.

Another useful class of anionic surfactants encompasses the water-soluble sulfated and sulfonated anionic ammonium, alkali-metal and alkaline earth metal detergent salts containing a hydrophobic higher alkyl moiety (typically containing from about 1 to 22 carbon atoms), such as salts of alkyl mono or polynuclear aryl sulfonates having from about 1 to 16 carbon atoms in the alkyl group (e.g., sodium toluene sulfonate, sodium xylene sulfonate, sodium dodecylbenzenesulfonate, magnesium tridecylbenzenesulfonate, lithium or potassium pentapropylenebenzenesulfonate). These compounds are available as Nacconol TM 35 SL (Stephan Chemical Co., Northfield, IL, sodium dodecylbenzene sulfonate) or as Stephanate TM X (sodium xylene sulfonate) or Stephanate TM AM (ammonium xylene sulfonate, Stephan Chemical Co.). The alkali metal salts of alkyl naphthalene sulfonic acids (methyl naphthalene sulfonates) are available as Petro TM AA. Petrochemical Corporation.

Also useful are the sulfated higher fatty acid monoglycerides such as the sodium salt of the sulfated monoglyceride of coconut oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$–$C_{16}$-alpha-olefin sulfonates such as the Bio-Terge TM series (Stephan Chemical Co.); alkali metal salts of higher fatty esters of low molecular weight alkyl sulfonic acids, e.g., fatty acid esters of the sodium salt of isethionic acid; the fatty ethanolamide sulfates; the fatty acid amides of amino alkyl sulfonic acids, e.g., lauric acid amide of taurine, and the alkali metal salts of sulfosuccinic acid esters, e.g., dioctyl sodium sulfosuccinate (Monawet TM series, Mona Industries, Inc., Patterson, NJ).

Preparation

The method of the present invention may be accomplished by mixing, in any order, the enzyme, the fatty acid salt, the solvent, and the surfactant if any, followed by the removal of the solvent. In the preferred method of the present invention, in order to ensure homogeneous mixing, one or more enzymes are first dry blended with the fatty acid salt, and then the dry blend is dispersed in the solvent. The dry blending may be achieved using commercially-available equipment. An example of such an apparatus in the P-K Twin Shell TM laboratory shaker manufactured by Patterson-Kelley Co., Inc., East Stroudsburg, Pa. There is no particular length of time required for conducting the mixing so long as the enzyme and the fatty acid salt components are thoroughly blended. Typically, the mixing is conducted from about 5 minutes to about 60 minutes, and preferably from about 15 minutes to about 45 minutes.

Preferably the weight ratio of enzyme component to fatty acid salt in the mixture is about 10-0.1:1, most preferably about 20-0.5:1. For example, an enzyme:-fatty acid salt ratio of a 1.0-0.5:1.0 is preferred when aluminum dioleate is employed as the fatty acid salt, and a ratio of 1.5-1.0:1 is preferred when aluminum distearate is employed.

The volume of solvent is determined on a v/w (volume/weight) ratio based on the combined weight of the enzyme and the fatty acid salt. Sufficient solvent must be employed to wet the enzyme and fatty acid salt. This can require a solvent volume/weight ratio of at least about 1:1 v/w. or more, e.g., about 10-1:1, preferably about 5-1:1. For example, when the solvent is acetone and the fatty acid salt is aluminum dioleate, an about 2-1:1 v/w ratio of solvent to enzyme and salt can be employed. On the other hand, when aluminum distearate is employed with acetone, an about 2.5-1.5:1 v/w ratio of solvent to enzyme and salt can be employed.

In order to ensure homogeneous distribution of the optional surfactant throughout the complex, the surfactant may be premixed in the solvent so that the solvent contains surfactant in an amount of up to about 10% by weight based on the combined weight of enzyme and fatty acid salt components. The surfactant may also be added during or after the mixing of the enzyme, the fatty acid salt, and the solvent.

Preferably, the surfactant is employed in an amount from about 0.1-5% by weight of the enzyme-fatty acid salt mixture, most preferably about 0.5-5%. For example, it has been found that when aluminum dioleate is employed, about 1% to 2% surfactant is preferably employed, whereas when the fatty acid salt is aluminum distearate, about 1% to 4% surfactant is preferably employed.

Following admixture of the enzyme, fatty acid salt, solvent and any surfactants, the solvent is removed. For example, solvent can be evaporated via a rotary vacuum dryer equipped with an internal scraper. Preferably, the solvent removal step is accomplished at ambient temperatures, in order to avoid thermal deactivation of the enzyme. Removal of the solvent yields a solid which may be ground in a general purpose mill to yield a finer granulation. No particular particle size is necessary for the finished composition, as it is only desirable to provide a substantially uniform particle size.

The invention will be further described by reference to the following detailed examples, wherein the enzyme mixture used in Examples I-IV was a 1:1 mixture of New Sumyzyme TM and Lipase-MY TM. New Sumyzyme TM (Shin Nihon Chemical Company, Japan) is a dry granulation of amyloglucosidase (AG) produced by Rizopus species. Lipase-MY TM. (Meito Sangyo Company, Japan) is a dry granulation of lipase produced by Candida cylindracea. Equal amounts by weight of the two enzymes were mixed for 30 minutes using a P-K Twin Shell TM Laboratory shaker apparatus (manufactured by Patterson-Kelley Co., Inc., East Stroudsburg, Pa.).

The aluminum dioleate (Alumagel TM) and aluminum distearate (Aluminum Stearate #22 TM) used in the Examples hereinbelow were supplied by Witco Chemical Corporation Organics Division, Chicago, Ill.

In the Examples hereinbelow, the activity of the amyloglucosidase (AG) was measured using the Diazyme TM Assay Method, Miles Laboratories, Inc. Technical Bulletin No. L-1042. This assay is based on the Schoorl method, a copper reduction method employing Fehling solution. One Diazyme TM Unit (DU) is that amount of amyloglucosidase that will liberate 1 g of reducing sugar as glucose per hour under the conditions of the assay. The activity was calculated as DU/g of amyloglucosidase unless otherwise indicated.

The activity of the lipase was measured using the Esterase Assay Method, Miles Laboratories, Inc., Technical Bulletin No. MM-800.17, which is based on the method described in Food Chemicals Codex, 3rd ed., National Academic Press, Washington, D.C. (1981). One Esterase Unit (EU) is defined as the activity that releases 1.25 micromoles of butyric acid per minute under the conditions of the assay. The activity was calculated as EU/g of lipase unless otherwise indicated.

EXAMPLE I

Amyloglucosidase/Lipase Mixture Modified with Aluminum Dioleate

A mixture of 75 g of New Sumyzyme TM amyloglucosidase (AG) and Lipase-MY TM lipase in a weight ratio of 1:1 was dry blended with 100 g of aluminum dioleate employing a P-K Twin Shell shaker for 30 minutes. Acetone (263 ml) was added to the resultant dry blend with stirring. The resultant slurry was then dried in a rotary vacuum dryer equipped with an internal scraper at room temperature for 60 minutes. The acetone solvent evaporated and was recovered by a condenser that had been attached to the vacuum line of the dryer.

The dried enzyme-aluminum dioleate complex was then around in a general purpose mill to a particle size of about 20 mesh on the U.S. mesh series (about 850 micometers) to rid the product of lumps and provide a fine granulation. About 175 g of the finished composition were recovered.

The resultant granules exhibited an activity of:
Amyloglucosidase—55 DU/g of granules,
Lipase—320 EU/g of granules.

EXAMPLE II

Amyloglucosidase/Lipase Mixture Modified with Aluminum Dioleate and Surfactant

Example I was repeated except that Neodol TM 25-3, an ethoxylated nonionic surfactant supplied by Shell Chemical Company, was added to the acetone by thoroughly mixing 1.75 g of the surfactant and 263 ml of acetone. The amount of the surfactant used was 1% of the 175 g weight of dry blend of enzymes and aluminum dioleate. The surfactant-containing acetone was used for slurrying the dry blend. Evaporation of the acetone provided a dry composition including the enzymes, aluminum dioleate and surfactant.

After grinding the composition on the general purpose mill to rid it of lumps, about 175 g of fine dry granules were recovered. The resultant granules exhibited an activity of:
Amyloglucosidase—55 DU/g of granules,
Lipase—320 EU/g of granules.

EXAMPLE III

Amyloglucosidase/Lipase Mixture Modified with Aluminum Distearate

The procedure of Example I was repeated, wherein the enzyme mixture of New Sumyzyme TM and Lipase-MY TM was dry blended on the P-K Twin Shell shaker with aluminum distearate on a 1.0:0.75 dry weight/weight ratio for 30 minutes. Thus, 100 g of enzyme mixture and 75 g aluminum distearate were combined to yield 175 g of dry blend which was then slurried in 350 ml of acetone. After slurrying, the acetone was evaporated.

After grinding the composition on the general purpose mill to rid it of lumps, fine dry granules of product were recovered. The resultant granules had an activity of:

Amyloglucosidase—74 DU/g of granules,
Lipase—425 EU/g of granules.

EXAMPLE IV

Amyloglucosidase/Lipase Mixture Modified with Aluminum Distearate and Surfactant The procedure of Example III was repeated except that the 175 g dry blend of enzymes-aluminum distearate was slurried in 350 ml of a solution of 3.5 g of Neodol TM 25-3 in 350 ml of acetone. The amount of surfactant used was 2% of the 175 g weight of the dry blend of aluminum distearate and enzymes. After slurrying, the acetone was evaporated to provide a dry solid which was milled to afford about 175 g of fine granules of product. The resultant granules had an activity of:

Amyloglucosidase—74 DU/g of granules,
Lipase—425 EU/g of granules.

EXAMPLE V

Comparative Enzyme Release

A. Amyloglucosidase Modified with Aluminum Dioleate and 0 to 2% Surfactant

Five portions of a dry blend of 175 g of New Sumyzyme TM (AG) and aluminum dioleate, on a 1.0:0.75 w/w ratio basis of enzyme to fatty acid salt were each slurried in 263 ml portions of acetone. The amount of Neodol TM surfactant pre-mixed into the five 263 ml aliquots of acetone was 0, 0.25, 0.5, 1.0 and 2.0% of the weight of the dry blend.

The enzymatic activity of samples of each of the resultant granular products was measured by adding eight 0.4 g samples of product to 9.6 ml portions of water. Samples 1-4 were left quiescent for 10, 20, 40 and 60 minutes, respectively, and samples 5-8 were mixed by shaking for 10 minutes on a Vortex-Genie TM apparatus (Scientific Industries, Inc., Bohemia, NY) at increasing speeds represented by settings No. 2, No. 4, No. 6 and No. 8 of the apparatus, respectively.

After the specified contact time, each of the eight samples was then filtered using Sharkskin TM analytical filter paper (Schleicher and Schuell, Inc., Keene, NH). The variance among the samples in the rate of extraction or leaching of the enzyme from the complex into the water was ascertained by measuring the activity of each filtrate, using the Diazyme Assay Method. The results are summarized on Table A, below.

TABLE A

Enzymatic Activity of Aluminum Dioleate-Modified AG Composition at Various Levels of Surfactant

| Sample No. | Static Contact Time | Neodol TM 25-3 Surfactant | | | | |
|---|---|---|---|---|---|---|
| | | 0% | 0.25% | 0.5% | 1.0% | 2.0% |
| 1 | 10 min. | 70.6* | 133.7 | 203.9 | 212.8 | 237.8 |
| 2 | 20 min. | 94.9 | 158.0 | 214.7 | 232.8 | 247.5 |
| 3 | 40 min. | 112.5 | 176.9 | 221.7 | 242.9 | 259.9 |
| 4 | 60 min. | 126.5 | 195.8 | 240.5 | 254.5 | 266.0 |
| | Mixing (10 min.) at Speed (No.) | | | | | |
| 5 | 2 | 186.0 | 197.2 | 240.1 | 248.3 | 268.1 |
| 6 | 4 | 198.3 | 207.9 | 248.3 | 257.4 | 277.4 |
| 7 | 6 | 207.4 | 228.4 | 259.8 | 271.8 | 286.7 |
| 8 | 8 | 234.9 | 240.5 | 273.9 | 277.7 | 295.4 |
| AG Control Solution | — | 260.0 | — | — | — | — |

*Activity of the composition (DU/q of AG) at various levels of surfactant was measured by determining the activity of the AG solubilized from the compositions at the given solubilization conditions.

The data summarized on Table A establish that the aluminum dioleate substantially retards the rate of solubilization of the AG enzyme into an aqueous medium. For example, a sample of complex which did not include surfactant yielded an aqueous phase having only about 27% of the enzymatic activity of a solution of the same amount of the free enzyme.

Furthermore, the rate of enzyme solubilization increased if either the mixing speed or the percentage of Neodol TM surfactant is increased. For instance, the activity of the sample with no Neodol TM mixed at a fast speed (setting No. 8) was about the same as the activity of the sample with 1% Neodol TM which was exposed to water with no agitation for 20 minutes.

Although the enzymatic activity of the aqueous phase could be increased by stirring the complex, 10 minutes of stirring at setting No. 8 was required to increase the activity of the aqueous phase to 90% of the activity exhibited by the control solution.

Addition of the surfactant substantially increased the rate of release of enzyme from the complex. For example, the addition of about 0.25-2.0% of Neodol TM 25-3 resulted in release of a major proportion of the activity after 10 minutes, whether or not the samples were agitated. Even static contact resulted in the substantially complete release of the enzymatic activity after 0.6-1.0 hour in the case of samples containing 1-2% of surfactant.

Thus, on a large industrial scale where physical mixing to increase the rate of dispersion of the enzyme may not be feasible, employing a surfactant in the present compositions with no mixing can achieve substantially the same result as employing the surfactant-free composition in an agitated aqueous medium.

B. Amyloglucosidase Modified with Aluminum Distearate and 0 to 4% Surfactant

The procedure of Example V(A) was repeated employing New Sumyzume TM (AG) and aluminum distearate in a 1.0:0.75 w/w ratio basis of enzyme to fatty acid salt. Thus, to prepare each sample, 175 g of the amyloglucosidase-aluminum distearate mixture were slurried in 350 ml aliquots of acetone. Also, the amount of Neodol TM 25-3 surfactant premixed into the acetone was varied incrementaly from 0% to 4% of the weight of dry blend of AG and aluminum stearate. As in Example V, the activity of each filtrate was measured by the Diazyme Assay Method.

The results are summarized in Table B below.

TABLE B

Enzymatic Activity of Aluminum Distearate-Modified AG Composition at Various Levels of Surfactant

| Sample No. | Static Contact Time | Neodol ™ 25-3 Surfactant | | | | | | |
|---|---|---|---|---|---|---|---|---|
| | | 0% | 0.25% | 0.5% | 1.0% | 2.0% | 3.0% | 4.0% |
| 1 | 10 min. | 32.0* | 41.8 | 31.5 | 50.4 | 153.5 | 184.3 | 218.9 |
| 2 | 20 min. | 38.3 | 47.9 | 40.4 | 56.5 | 177.3 | 207.7 | 231.0 |
| 3 | 40 min. | 43.8 | 51.6 | 48.7 | 61.1 | 239.6 | 249.2 | 250.6 |
| 4 | 60 min. | 26.5 | 61.3 | 57.1 | 66.3 | 270.4 | 267.9 | 260.1 |
| | Mixing (10 min.) at Speed (No.) | | | | | | | |
| 5 | 2 | 77.5 | 68.1 | 94.2 | 101.3 | 278.6 | 270.2 | 278.9 |
| 6 | 4 | 127.9 | 137.2 | 137.0 | 144.4 | 289.1 | 281.4 | 288.6 |
| 7 | 6 | 142.6 | 184.6 | 186.0 | 173.8 | 295.1 | 290.2 | 298.2 |
| 8 | 8 | 195.1 | 229.4 | 231.0 | 244.0 | 301.5 | 301.8 | 298.7 |

*Activity of the composition (DU/g of AG) at different levels of surfactant was measured by determining the activity of the AG solubilized from the composition at the given solubilization conditions.

The data summarized in Table B also demonstrate that the rate of enzymatic release increased as the percentage of surfactant increased and/or the ten minute mixing speed increased. However, the aluminum distearate-containing samples prepared in accordance with this example required more Neodol ™ surfactant than did the aluminum dioleate-containing samples assayed in Example V(A) (2% Neodol ™ surfactant for aluminum distearate modified AG versus 1% Neodol ™ surfactant for aluminum dioleate modified AG) to obtain an equivalent degree of solubility.

EXAMPLE VII

Properties of AG/Lipase Modified with Aluminum Dioleate

The compositions of Example I are evaluated with respect to their ability to degrade greasy soil as follows. First, 20 grams of greasy material from a grease trap is placed in 100 ml of 30° C. water in a 200 ml beaker. Then, 0.25 g of the composition of Example I are added thereto with stirring. For comparison, a sample containing 20 grams of the greasy substance and 0.11 g of unmodified AG/lipase (0.11 g is used since the 0.25 g of modified AG/lipase comprises about 0.11 g of enzymes and about 0.14 g of salt) in 100 ml of 30° C. water is also prepared. The test mixtures and the control mixture (no enzyme) are maintained at 30° C. In the sample beakers, the modified enzyme-containing granules immediately associate with the layer of the oil, while the free enzymes dissolved in the water. A lipolytic reaction in the sample beakers is noticeable in about 24 hours and thus both beakers (modified and free enzyme) are visually evaluated after 1 day and 2 days. The results of this study are summarized in Table C below.

TABLE C

| Sample | Comparative Degradation of Oil | |
|---|---|---|
| | 24 Hours | Two Days |
| Control | a. All the greasy substance is settled on bottom of beaker. | a. Same |
| | b. Supernatant is clear. | b. Same |
| Free Enzyme-Containing Sample | a. Some sediment is on bottom of beaker. | a. Less sediment is on bottom of beaker. |
| | b. There is a loosely packed surface layer of greasy substance having small gas bubbles. | b. There is some packing of upper layer with more gas bubbles. |
| | c. Supernatant is slightly turbid. | c. Supernatant is turbid. |
| Lipophilic Enzyme-Containing Composition | a. Some sediment is on bottom of beaker. | a. Less sediment is on bottom of beaker. |
| | b. There is a packed surface layer of greasy substance having gas bubbles. | b. There is more packing of upper layer with more gas bubbles. |
| | c. Supernatant is turbid. | c. Supernatant is more turbid. |

The data summarized on Table C indicate that the lipase-containng composition of the present invention can substantially degrade soil comprising fat and grease in aqueous media under static conditions, and can do so more effectively than an equivalent amount of enzymes which are simply dissolved in the medium. It is believed that this result is due both to the enhanced association between the hydrophobic fatty-acid enzyme complex and the gradual release of the enzyme therefrom, which effectively enhances its stability.

While certain representative embodiments of the invention have been described herein for purposes of illustration, it will be apparent to those skilled in the art that modifications therein may be made without departing from the spirit and scope of the invention.

What is claimed is:

1. An enzyme-containing composition formed by a process comprising:
   (a) forming a mixture comprising a water-soluble enzyme selected from the group consisting of amyloglucosidase, lipase, and mixtures thereof, a water-insoluble metal salt of a fatty acid, of the general formula:

$$(RCO_2^-)_y (^-OH)_x (M^{x+y})$$

wherein R is an alkyl group having from 6 to 30 carbon atoms and from 0-3 double bonds, x is 0-2, y is 1-3 and $M^{x+y}$ is $Al^{+3}$, $Mg^{+2}$ or $Ca^{+2}$, and an organic solvent;
   (b) removing the organic solvent from the mixture to yield a solid composition which is substantially less hydrophilic than said water soluble enzyme.

2. The composition of claim 1 wherein the solid composition is immiscible in water.

3. The composition of claim 1 wherein the enzyme gradually dissociates from the solid composition in the presence of an excess of water.

4. The composition of claim 1 wherein the weight ratio of enzyme to fatty acid salt is about 10-0.1:1.

5. The composition of claim 1 wherein the volume:weight ratio of solvent to the combined weight of the fatty acid salt and the enzyme is at least about 1:1.

6. The composition of claim 5 wherein the volume:weight ratio of solvent to the fatty acid salt and the enzyme is about 10-1:1.

7. The composition of claim 1 wherein the mixture further comprises a nonionic surfactant, an anionic surfactant, or mixtures thereof, in an amount effective to substantially increase the dissociation rate of the enzyme from the solid composition.

8. The composition of claim 7 wherein the mixture comprises a nonionic surfactant.

9. The composition of claim 7 wherein about 0.5-5% by weight of the enzyme and the fatty acid salt of the surfactant is incorporated into the mixture.

10. An enzyme containing composition formed by a process comprising:
(a) forming a mixture comprising a water-soluble enzyme selected from the group consisting of amyloglucosidase, lipase and mixtures thereof, a water-insoluble fatty acid metal salt of the general formula:

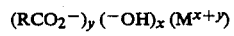

wherein R is a $C_6-C_{30}$ alkyl group containing 0-3 double bonds, x is 0-2, y is 1-3 and $M^{x+y}$ is $Al^{+3}$, $Mg^{+2}$ or $Ca^{+2}$; and an organic solvent selected from the group consisting of alcohols, ketones, aromatics, alkyl halides and ethers; wherein the weight ratio of enzyme to fatty acid metal salt is about 2-0.5:1 and the volume:weight ratio of solvent to enzyme-salt is about 10-1:1; and
(b) removing the organic solvent from the mixture to yield a solid composition.

11. The composition of claim 10 wherein R is a $C_8-C_{22}$ alkyl group.

12. The composition of claim 11 wherein the fatty acid metal salt is an oleate, a stearate or a palmitate.

13. The composition of claim 10 wherein the mixture further comprises about 0.1-5% by weight of the enzyme-fatty acid salt mixture of a nonionic surfactant, an anionic surfactant or a mixture thereof.

14. An enzyme-containing composition formed by a process comprising:
(a) forming a mixture comprising a water soluble enzyme selected from the group consisting of amyloglucosidase, lipase and mixtures thereof, a water insoluble fatty acid metal salt of the general formula:

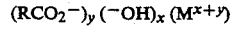

wherein y is 1-3, x is 0-1 and $M^{x+y}$ is $Al^{+3}$, $Mg^{+2}$ or $Ca^{+2}$ and a ketone solvent; wherein the weight ratio of enzyme to fatty acid metal salt is about 2-0.5:1 and the volume:weight ratio of solvent to enzyme-salt is about 5-1:1; and (b) removing the organic solvent from the mixture to yield a solid composition.

15. The composition of claim 14 wherein the fatty acid metal salt is aluminum distearate or aluminum dioleate.

16. The composition of claim 14 wherein the solvent is acetone.

17. The composition of claim 14 wherein the mixture comprises about 0.5-5% by weight of the enzyme-fatty acid mixture of a nonionic surfactant.

18. The composition of claim 17 wherein the nonionic surfactant comprises the condensation product of a $C_8-C_{22}$ alkyl alcohol with about 2-50 moles of ethylene oxide.

19. The composition of claim 18 wherein the nonionic surfactant comprises the condensation product of a $C_{12}-C_{15}$ alkyl alcohol with about 3-9 moles of ethylene oxide.

20. A process for reducing the hydrophilicity of a water-soluble enzyme comprising:
(a) forming a mixture comprising a water-soluble enzyme selected from the group consisting of amyloglucosidase, lipsase and mixtures thereof, a water-insoluble metal salt of a fatty acid of the general formula:

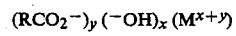

wherein y is 1-3, x is 0-1 and $M^{x+y}$ is $Al^{+3}$, $Mg^{+2}$ or $Ca^{+2}$, and an organic solvent;
(b) removing the organic solvent from the mixture to yield a solid composition which is substantially less hydrophilic than said enzyme.

21. The process of claim 20 wherein the weight ratio of enzyme to fatty acid salt is about 10-0.1:1.

22. The process of claim 21 wherein the volume:weight ratio of solvent to the combined weight of the fatty acid salt and the enzyme is at least about 1:1.

23. The process of claim 22 wherein the volume:weight ratio of solvent to the fatty acid salt and the enzyme is about 10-1:1.

24. The process of claim 22 wherein the mixture further comprises a nonionic surfactant, an anionic surfactant, or mixtures thereof, in an amount effective to substantially increase the dissociation rate of the enzyme from the solid composition.

25. The composition of claim 24 wherein about 0.1-5% by weight of the enzyme and the fatty acid salt of the surfactant is incorporated into the mixture.

* * * * *